United States Patent [19]

Heumüller et al.

[11] Patent Number: 5,266,668
[45] Date of Patent: Nov. 30, 1993

[54] SUBSTITUTED PHENYL α-FLUOROACRYLATES

[75] Inventors: Rudolf Heumüller, Rodgau; Peter Herbrechtsmeier, Köngistein/Taunus; Günter Siegemund, Hofheim am Taunus; Werner Groh, Frankfurt am Main, all of Fed. Rep. of Germany

[73] Assignee: Hoechst Aktiengesellschaft, Frankfurt am Main, Fed. Rep. of Germany

[21] Appl. No.: 43,623

[22] Filed: Apr. 7, 1993

Related U.S. Application Data

[63] Continuation of Ser. No. 867,296, Apr. 10, 1992, abandoned, which is a continuation of Ser. No. 707,021, May 29, 1991, abandoned, which is a continuation of Ser. No. 61,795, Jun. 11, 1987, abandoned.

[30] Foreign Application Priority Data

Jun. 14, 1986 [DE] Fed. Rep. of Germany ....... 3620050

[51] Int. Cl.$^5$ ............................................. C08F 18/20
[52] U.S. Cl. .................................................... 526/245
[58] Field of Search ........................................ 526/245

[56] References Cited

U.S. PATENT DOCUMENTS 2,877,207  3/1959  Cox et al. .
4,259,407  3/1981  Tada et al. .
4,297,466  10/1981  Bloch et al. .
4,323,695  4/1982  Bloch et al. ........................ 526/245
4,572,805  2/1986  Kaieda et al. .
4,604,482  8/1986  Ohmori et al. .

FOREIGN PATENT DOCUMENTS 0128517  12/1984  European Pat. Off. .
1115287  5/1968  United Kingdom ................ 526/245

OTHER PUBLICATIONS

Ishikawa, N. et al., *J. Fluorine Chemistry* 25:203–212 (1984).

*Primary Examiner*—Joseph L. Schofer
*Assistant Examiner*—N. Sarofim
*Attorney, Agent, or Firm*—Connolly & Hutz

[57] ABSTRACT

Certain esters of α-fluoroacrylic acid are accessible by hydrolyzing α-hydroxymethyl α-fluoromalonic acid esters and subsequently decarboxylating the hydrolysis product. The phenyl α-fluoroacrylates which are substituted on the phenyl radical can be prepared by hydroxymethylating dimethyl α-fluoromalonate, decarboxylating and dehydrating the resuiting dimethyl α-hydroxymethyl-α-fluoromalonate and esterifying the resuiting α-fluoroacrylic acid with substituted phenols. The substituted phenyl α-fluoroacrylates are colorless liquids or colorless solids which can be polymerized. They are suitable for use as a starting material for the preparation of fluorine polymers.

5 Claims, No Drawings

SUBSTITUTED PHENYL α-FLUOROACRYLATES

CROSS-REFERENCE TO RELATED APPLICATIONS

This application is a continuation of Ser. No. 07/867,296, filed on Apr. 10, 1992, now abandoned, entitled "Substituted Phenyl Alpha-Fluoroacrylates" in the names of Rudolf Heumuller, Peter Herbrechtsmeir, Gunter Siegemund and Werner Groh, which was a continuation of Ser. No. 07/707,021, filed May 29, 1991, now abandoned, which was a continuation of Ser. No. 07/061,795 filed Jun. 11, 1987, now abandoned, by the same inventors.

The invention relates to esters of α-fluoroacrylic acid with substituted phenols, a process for the preparation of these esters and their use.

BACKGROUND OF THE INVENTION

Esters of α-fluoroacrylic acid are already known. Thus the phenyl ester of α-fluoroacrylic acid is prepared by reacting ethyl monofluoroacetate in the presence of sodium ethylate with ethyl oxalate, converting the sodium α-fluoroacrytate obtained into a-fluoroacryloyl chloride by means of thionyl chloride and then esterifying this product with phenol (German Patent No. 2,950,491=U.S. Pat. No. 4,297,466). It is a disadvantage in this process that ethyl monofluoroacetate, which is highly toxic, has to be employed. Phenyl α-fluoroacrylate can be polymerized and is used for the preparation of polymers which, at room temperature, are translucent or transparent or light-transmissive, colorless solids.

Other esters of α-fluoroacrylic acid, in particular butyl α-fluoroacrylate, can be prepared by acid hydrolysis of the appropriate α-hydroxymethyl-α-fluoromalonate followed by decarboxylation of the hydrolysis product with simultaneous elimination of alcohol (British Patent No. 1,115,287). This method is, however, only described for the example of butyl α-fluoroacrylate; the ester rapidly polymerizes under the influence of light.

SUMMARY OF THE INVENTION

Polymers of fluorinated acrylic acid esters are also known, which correspond to the formula $RHC=CR-CO-OR_1$ in which R is a hydrogen atom, a methyl group or a halogen atom and $R_1$ is a fluorinated alkyl or aryl radical (U.S. Pat. No. 2,877,207); the fluoroalkyl radical of the alcohol component is, in particular, a radical containing two hydrogen atoms on the carbon atom in the 1-position and no detailed statements at all are made in which R denotes a halogenoalkyl group having 1 to 8 carbon atoms and p is nought, 1, 2 or 3, X denotes a halogen atom and n is nought or an integer from 1 to 5 (it being possible for X to denote different halogen atoms if n is greater than 1), Y denotes a hydrogen atom, a cyano group, the radical X or the radical R and m is nought or 1, the sum of n +m +p denoting 1 to 5.

The invention also relates to a process for the preparation of a substituted phenyl α-fluoroacrylate, which comprises reacting dimethyl α-fluoromalonate with formaldehyde in a first process stage, then hydrolyzing, decarboxylating and dehydrating the resuiting hydroxymethylated dimethyl α-fluoromalonate in a second process stage and subsequently, in a third process stage, esterifying the resuiting α-fluoroacrylic acid (if appropriate in the form of an acid halide) with a phenol of the formula (2)

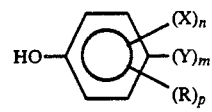

in which X, Y, R, n, m and p have the meaning indicated in formula (1) (if appropriate in the form of an alkali metal phenate).

Finally, the invention also relates to the use of substituted phenyl α-fluoroacrylates of the formula (1) as a starting material for the preparation of polymers containing fluorine.

The process according to the invention is carried out in three stages: dimethyl α-fluoromalonate is first reacted with formaldehyde to give dimethyl α-hydroxymethyl-α-fluoromalonate, the latter is then hydrolyzed and the hydrolysis product is decarboxylated and dehydrated, and finally, the resuiting α-fluoroacrylic acid is esterified with a substituted phenol.

In the first process stage, dimethyl α-fluoromalonate is subjected to hydroxymethylation with formaldehyde. (Dimethyl α-fluoromalonate is a known compound; see Journal of Fluorine Chemistry 25 (1984), 203–212.) The formaldehyde is preferably employed in the form of an aqueous solution having a formaldehyde content of 30 to 40% by weight. The formaldehyde is employed in an amount of 1 to 10 mot, preferably 1.1 to 3 mot (relative to 1 mol of dimethyl α-fluoromalonate). It is also possible to use paraformaldehyde, hexamethylenetetramine or 1,3,5-trioxane instead of formaldehyde. It is advantageous to carry out the reaction in the presence of a basic catalyst, which is then used in an amount of 2 to 50, preferably 5 to 15, mol % (relative to the dimethyl α-fluoromalonate). The catalyst used is, in particular, an alkali metal bicarbonate, for example potassium bicarbonate and sodium bicarbonate. The reaction is carried out at a temperature of 5° to 40° C., preferably 15° to 30° C. The dimethyl α-hydroxymethyl-α-fluoromalonate formed is then isolated from the reaction mixture, preferably by salting out or extraction by means of a water-immiscible organic solvent. A suitable solvent is, above all, an aliphatic chlorinated hydrocarbon having 1 to 4 carbon atoms, for example methylene dichloride, chloroform, carbon tetrachloride, 1,1-dichloroethane or 1,2-dichloroethane. A combination of salting out and extraction is particularly advantageous; a saturated salt solution (ammonium sulfate or sodium chloride) is then first added to the reaction mixture, and this mixture is then extracted. Dimethyl α-hydroxymethyl-α-fluoromalonate is obtained in the form of a colorless solid by evaporating the solvent.

In the second process stage, the dimethyl α-hydroxymethyl-α-fluoromalonate is hydrolyzed in an aqueous acid medium, and the hydrolysis product is decarboxylated and dehydrated. The reaction is carried out at a pH from −1 to 6, preferably 0 to 2; the acid medium is prepared by means of an aqueous acid solution, preferably a dilute inorganic acid, such as hydrochloric acid or sulfuric acid. The reaction temperature is within the range from 90° to 110° C., preferably 95° to 105° C. When the evolution of gas is complete, the reaction mixture is distilled under a pressure of 1013 to 600 mbar, and the distillate is extracted with an organic solvent. The solvent used here is also a water-immiscible solvent, preferably an ether, such as diethyl ether. α-fluoroacrylic acid is obtained in the form of a colorless solid after the solvent has been removed by evaporation. In a preferred variant, the α-fluoroacrylic acid is isolated in the form of its ammonium salt. This is effected by passing gaseous ammonia through the solution obtained after the extraction, and then freeing the colorless crystalline precipitate from the solvent.

In the third process stage, the α-fluoroacrylic acid is esterified with a substituted phenol. The phenol is employed in an amount of 0.5 to 1.5 mol, preferably 0.8 to 1.2 mol (relative to 1 mol of α-fluoroacrylic acid). In some cases—if the acid is employed in the form of a halide—the phenol is employed in the form of an alkali metal phenate, preferably sodium phenate or potassium phenate. The α-fluoroacrylic acid is employed for the esterification as such or, preferably, in the form of an acid halide, in particular as α-fluoroacryl chloride. The acid halide is prepared by means of a customary halogenating agent, for example oxalyl chloride, phosphorus pentachloride, phosphorus trichloride, phosphorus oxychloride, benzoyl chloride, benzotrichloride, phosphorus tribromide, sulfur tetrafluoride and, especially, thionyl chloride. The halogenation by means of thionylchloride is preferably carried out in the presence of a catalyst, such as dimethyl formamide. The reaction is carried out in an aromatic hydrocarbon, for example toluene, xylene and trimethylbenzene, as the solvent, and the reaction temperature is within the range from 50° to 100° C., preferably 70° to 90° C.

The esterification is preferably carried out in a solvent and the reaction temperature in this case is −10° to 50° C., preferably 0° to 25° C. The solvent used is a polar organic solvent, in particular a symmetrical, asymmetrical or cyclic ether, for example diethyl ether, dipropyl ether, diisopropyl ether, tert.-butyl methyl ether, tetrahydrofuran and dioxane, and aliphatic halogenated hydrocarbon, preferably a chlorinated hydrocarbon, for example methylene dichloride, chloroform, carbon tetrachloride, 1,1-dichloroethane and 1,2-dichloroethane, an aromatic halogenatic hydrocarbon, preferably a chlorinated hydrocarbon, for example chlorobenzene and 1,2-dichlorobenzene or 1,3-dichlorobenzene, or an aliphatic or aromatic nitrite, for example acetonitrile and benzonitrite. The solvent can also be a mixture of several polar solvents. It is expedient to carry out the esterification of the acid halide with the phenol in the presence of an organic base, in particular a trialkylamine having 1 to 4 carbon atoms in each of the alkyl groups. The base is employed in an amount of 0.5 to 2 mol, preferably 0.8 to 1.2 mol (relative to 1 mol of acid halide). The resuiting substituted phenyl α-fluoroacrylate is isolated from the reaction mixture by distillation, preferably under a pressure of 1013 to 200 mbar, or—after the solvent has been removed by distillation by hot extraction of the solid residue with a nonpolar solvent, preferably an aliphatic hydrocarbon, such as n-hexane, and subsequent crystallization. It is expedient to carry out the distillation in the presence of a customary polymerization inhibitor, for example hydroquinone or hydroquinone monomethyl ether; this is used in an amount of 100 to 500 ppm (relative to α-fluoroacryloyl halide). The bottom temperature is within the range from 20° to 100° C., preferably 30° to 85° C. The phenyl ester is purified further by being distilled again, preferably under reduced pressure, or recrystallized. The substituted phenyl α-fluoroacrylates according to the invention carry 1 to 5, preferably 2 to 5, substituents on the phenyl radical; preferred esters are those which contain, as substituents or in the substituent, a fluorine atom or several fluorine atoms.

The esters according to the invention include, for example, the following compounds: 2- or 3- or 4-fluorophenyl α-fluoroacrylate, 2- or 3- or 4-chlorophenyl α-fluoroacrylate, 2- or 3- or 4-bromophenyl α-fluoroacrylate, 2- or 3- or 4-iodophenyl α-fluoroacrylate, 2,3- or 2,4- or 2,5- or 2,6- or 3,4- or 3,5-difluorophenyl α-fluoroacrylate, 2,3- or 2,4- or 2,5- or 2,6- or 3,4- or 3,5-dichlorophenyl α-fluoroacrylate, 2- or 3-chlor-4-fluorophenyl α-fluoroacrylate, 2-bromo-4-chlorophenyl α-fluoroacrylate, 4-bromo-2-chlorophenyl α-fluoroacrylate, 2,6-dibromo-4-fluorophenyl α-fluoroacrylate, 4-bromo-2,6-dichlorophenyl α-fluoroacrylate, 2,4-dichloro-6-iodophenyl α-fluoroacrylate, 2,3,4- or 2,3,5- or 2,3,6- or 2,4,5- or 2,4,6- or 3,4,5-trichloro-phenyl α-fluoroacrylate, 2,4,6-tribromophenyl α-fluoroacrylate, 2,4,6-triiodophenyl α-fluoroacrylate, 2,3,5,6-tetrafluorophenyl α-fluoroacrylate, 2,3,4,5-tetrachlorophenyl α-fluoroacrylate, 2,3,5,6-tetrachlorophenyl α-fluoroacrylate, pentafluorophenyl α-fluoroacrylate, pentachlorophenyl α-fluoroacrylate, pentabromophenyl α-fluoroacrylate, 2,6-diiodo-4-trifluoromethylphenyl α-fluoroacrylate, 2- or 3- or 4-trifluoromethylphenyl α-fluoroacrylate, 2-(heptafluoro-2-propyl)phenyl or 4-(heptafluoro-2-propyl)-phenyl α-fluoroacrylate, 2,6- or 3,5-bis(trifluoromethyl)-phenyl α-fluoroacrylate, 4-cyanophenyl α-fluoroacrylate, 2,6-dibromo-4-cyanophenyl α-fluoroacrylate, 2,6-dichloro-4-cyanophenyl α-fluoroacrylate, 2,6-difluoro-4-cyanophenyl α-fluoroacrylate, 4-cyano-2,3,5,6-tetrafluorophenyl α-fluoroacrylate, 4-chloro-2,5- (or 3,5)-difluorophenyl α-fluoroacrylate, 2-chloro-4,5- (or 4,6)-difluorophenyl α-fluoroacrylate, 2,5- or 2,6- or 3,5-dichloro-4-fluorophenyl α-fluoroacrylate, 2,6- or 3,4-dibromo-3,4 (or 2,6)-dichlorophenyl α-fluoroacrylate, 2,4,6-trichloro-3-fluorophenyl α-fluoroacrylate, 2,4- or 2,6-dichloro-3-trifluoromethylphenyl α-fluoroacrylate, 2,6-dibromo-4- (or 5) -trifluoromethylphenyl α-fluoroacrylate, 2,4-dibromo-5- (or 6)-trifluoromethylphenyl α-fluoroacrylate, 2- or 4-bromo-3- (or 5)-trifluoromethylphenyl α-fluoroacrylate, 2,3,6-tribromo,4,5-bis-bromomethylphenyl α-fluoroacrylate, 2,4,5-tribromo-3,6-bis-(bromomethyl)phenyl α-fluoroacrylate, 2,4,6-trichloro-3,5-bis(chloromethyl)phenyl) α-fluoroacrylate, 3,4,5-trichloro-2,6-bis(chloromethyl)phenyl α-fluoroacrylate, 2,4,6-trichloro-3-chloromethylphenyl α-fluoroacrylate, 2,4-dibromo-6-dibromomethylphenyl α-fluoroacrylate, 2,6-dibromo-4-dibromomethylphenyl α-fluoroacrylate, 2,3,5,6-tetrachloro-4-chloromethylphenyl α-fluoroacrylate, 2- or 3-fluoro-4-methylphenyl α-fluoroacrylate, 3- or 4- or 5-fluoro-2-methylphenyl α-fluoroacrylate, 2-fluoro-6-methylphenyl α-fluoroacrylate, 4-fluoro-3-methylphenyl α-fluoroacrylate, 2,4,6-trichloro-3,5-dimethylphenyl α-fluoroacrylate, 2,6-dichloro-3,5-dimethylphenyl α-fluoroacrylate, 2,6-dichloro-4-methylphenyl α-fluoracrylate, 2,4,6-tribromo-3,5-dimethylphenyl α-fluoroacrylate, 2,4,6-tribromo-3-methylphenyl α-fluoroacrylate, 2,3,5,6-tetrafluoro-4-cyanophenyl α-fluoroacrylate, 2- or 3- or 4-methylphenyl α-fluoroacrylate, 2,3- or 2,4- or 2,5- or 2,6- or 3,4- or 3,5-dimethylphenyl α-fluoroacrylate, 2,4,6-trimethylphenyl α-fluoroacrylate, 2,3,5,6-tetramethylphenyl α-fluoroacrylate, 2- or 3- or 4-isopropylphenyl α-fluoroacrylate, 4-isopropyl-3,5-dimethylphenyl α-fluoroacrylate and 2,3- or 2,5- or 2,6- or 3,4- or 3,5-diisopropylphenyl α-fluoroacrylate.

The substituted phenyl esters of α-fluoroacrylic acid are colorless liquids or colorless solids at room temperature. They are readily polymerizable and are suitable for the preparation of crystal clear, light-transmissive, colorless polymers.

The following examples serve to illustrate the invention in greater detail. Percentages relate in each case to weight.

EXAMPLE 1 a) 48 g (0.48 mol) of potassium bicarbonate were dissolved in 535 g (6.59 mol) of aqueous formaldehyde solution (37% strength by weight) in a 4-liter glass flask. 841 g (5.6 mol) of dimethyl α-fluoromalonate were added dropwise to this solution., with stirring, in the course of 3½ hours; the temperature was kept meanwhile within the range from 20° to 25° C. Stirring was continued for 2 hours at the same temperature, and during this time dimethyl α-hydroxymethyl-α-fluoromalonate was precipitated in the form of a colorless solid. 2,500 g of an aqueous, saturated solution of ammonium sulfate were then added to the reaction mixture, which was then extracted with methylene dichloride. The extraction solution was dried by means of anhydrous sodium sulfate. 906 g (90% of theory) of dimethyl a-hydroxymethyl-α-fluoromalonate were obtained after removing the methylene dichloride by distillation (bath temperature 40° C., 25 mbar).

b) 175 g (0.97 mol) of dimethyl α-hydroxymethyl-α-fluoromalonate, 750 ml of water and 750 ml of hydrochloric acid (36% strength by weight) were heated at the boil for 2½ hours in a 2-liter glass flask equipped with a thermometer and stirrer and a Vigreux column fitted with a distillation head. The temperature of the reaction mixture was 103° C. The reaction mixture was then distilled. 1 g of hydroquinone monomethyl ether was added to the distillate and the latter was extracted with diethyl ether, and the extraction solution was dried by means of anhydrous sodium sulfate. 17 g (1 mol) of gaseous ammonia were then passed into the solution at room temperature. The colorless precipitate obtained thereby was filtered off, washed with diethyl ether and dried at room temperature under reduced pressure. 70.8 g (68% of theory) of ammonium α-fluoroacrylate were obtained.

c) 100 g (0.934 mol) of ammonium α-fluoroacrylate were dispersed in a mixture of 600 g of mesitylene and 15 ml of dimethylformamide in a 1-liter glass flask and 119 g (1.0 mol) of thionyl chloride were added in the course of one hour. The resulting mixture was heated to a temperature of 80° C. and was kept at this temperature for 2 hours, with stirring. The liquid obtained after the mixture had cooled to room temperature was distilled under reduced pressure, and the fraction obtained up to 100° C./160 mbar was distilled again under normal pressure. 67 g (66% of theory) of α-fluoroacryloyl chloride were obtained, boiling point 65° to 67° C.

d) A solution of 111 g (0.5 mol) of potassium pentafluorophenate in 250 ml of anhydrous acetonitrile was added dropwise, in the course of 1 hour, at a temperature of 25° C. and with stirring, to a solution of 54.5 g (0.502 mol) of α-fluoroacryloyl chloride in 100 ml of anhydrous acetone nitrite, and the reaction mixture was then stirred for a further 2 hours at the same temperature. The solid formed was filtered off and washed with 100 ml of anhydrous acetonitrile. The mixture of filtrate and wash solution was distilled, after adding 0.01 g of hydroquinone monomethyl ether. 107.1 g (84% of theory) of penafluorophenyl α-fluoroacrylate were obtained, boiling point 41° to 42° C. (under 2 mbar).

EXAMPLE 2

13.9 g (0.128 mol) of α-fluoroacryloyl chloride (obtained in accordance with example 1c) were added dropwise, at a temperature of 25° C., with stirring and in the course of 30 minutes, to a solution of 30 g (0.0985 mol) of potassium pentachlorophenate in 400 ml of anhydrous acetonitrile, and the reaction mixture was then stirred for a further 90 minutes at the same temperature. The solid formed was filtered off and washed with 20 ml of anhydrous acetonitrile. After 0.01 g of hydroquinone monomethyl ether had been added, the volatile constituents in the mixture of filtrate and washing liquor were distilled off and the residue was recrystallized from boiling n-hexane. 17 g (51% of theory) of pentachlorophenyl α-fluoroacrylate were obtained, melting point 90° to 92° C.

EXAMPLE 3

49 g (0.181 mol) of 2,6-dibromo-4-fluorophenol were dissolved in 150 ml of anhydrous methylene dichloride, and 18.3 g (0.181 mol) of triethylamine were added to the solution; 20 g (0.184 mol) of (I-fluoroacryloyl chloride (obtained in accordance with example 1c) were then added dropwise at a temperature of 5° C., with stirring and in the course of 30 minutes, and the reaction mixture was stirred for a further 30 minutes at the same temperature. The solid formed was filtered off and washed with 30 ml of methylene dichloride. The mixture of filtrate and wash solution was distilled, after adding 0.01 g of hydroquinone monomethyl ether. 46 g (74% of theory) of 2,6-dibromo-4-fluorophenyl α-fluoroacrytate were obtained, boiling point 86° to 88° C. (under 0.4 mbar).

EXAMPLE 4

2.2 g (0.02 mol) of α-fluoroacryloyl chloride (obtained in accordance with example 1c) were added dropwise, at a temperature of 5° C., with stirring and in the course of 5 minutes, to a solution of 7.8 g (0.019 mol) of 2,6-diiodo-4-trifluoromethylphenyl and 2 g (0.02 mol) of triethylamine in 80 ml of anhydrous methylene dichloride, and the reaction mixture was then stirred for a further 30 minutes at the same temperature. The solid formed was filtered off and washed with 10 ml of anhydrous methylene dichloride. After 0.001 g of hydroquinone monomethyl ether had been added, the volatile constituents in the mixture of filtrate and wash solution were removed by distillation, and the residue was recrystallized from boiling in-hexane. 7 g (76% of theory) of 2,6-diiodo-4-trifluoromethylphenyl α-fluoroacrylate were obtained, melting point 93° to 95° C.

EXAMPLE 5

16.2 g (0.1 mol) of 4-trifluoromethylphenol were dissolved in 80 ml of anhydrous diethyl ether, and 10.1 g (0.1 mol) of triethylamine were added in portions to the solution; 12 g (0.11 mol) of α-fluoroacryloyl chloride (obtained in accordance with example 1c) were then added dropwise, at a temperature of 10° C., with stirring, and in the course of 20 minutes, and the reaction mixture was stirred for a further 60 minutes at the same temperature. The solid formed was filtered off and washed with 20 ml of diethyl ether. The mixture of filtrate and wash solution was distilled, after adding 0.005 g of hydroquinone monomethyl ether. 19.5 g (83% of theory) of 4-trifluoromethylphenyl α-fluoroacrylate were obtained, boiling point 69° to 70° C. (under 3 mbar).

EXAMPLE 6

27.5 g (0.169 mol) of 3-trifluoromethylphenol were dissolved in 100 ml of anhydrous methylene dichloride, and 17.1 g (0.169 mol) of triethylamine were added in portions to the solution; 20 g (0.184 mol) of α-fluoroacryloyl chloride (obtained in accordance with example 1c) were then added dropwise, at a temperature of 5° C., with stirring and in the course of 20 minutes, and the reaction mixture was stirred for a further 60 minutes at the same temperature. The solid formed was filtered off and washed with 30 ml of methylene dichloride. The mixture of filtrate and wash solution was distilled, after adding 0.01 g of hydroquinone monomethyl ether. 27 g (68% of theory) of 3-trifluoromethylphenyl α-fluoroacrylate were obtained, boiling point 78° to 79° C. (under 4 mbar).

EXAMPLE 7

26.2 g (0.1 mol) of 4-perfluoroisopropylphenol were dissolved in 100 ml of anhydrous diethyl ether, and 10.1 g (0.1 mol) of triethylamine were added to the solution; 12 g (0.11 mol) of α-fluoroacryloyl chloride (obtained in accordance with example 1c) were then added dropwise, at a temperature of 10° C., with stirring and in the course of 15 minutes, and the reaction mixture was stirred for a further 30 minutes at the same temperature. The solid formed was filtered off and washed with 20 ml of diethyl ether. The mixture of filtrate and wash solution was distilled, after adding 0.005 g of hydroquinone monomethyl ether. 22.9 g (69% of theory) of 4-perfluoroisopropylphenyl α-fluoroacrylate were obtained, boiling point 65° to 66° C. (under 1 mbar).

EXAMPLE 8

10 g (0.038 moo of 2-perfluoroisopropylphenol were dissolved in 30 ml of anhydrous diethyl ether, and 3.9 g (0.038 mol) of triethylamine were added to the solution; 4.3 g (0.039 mol) of α-fluoroacryloyl chloride (obtained in accordance with example 1c) were then added dropwise, at a temperature of 10° C., with stirring and in the course of 12 minutes, and the reaction mixture was stirred for a further 30 minutes at the same temperature. The solid formed was filtered off and washed with 10 ml of diethyl ether. The mixture of filtrate and wash solution was distilled after adding 0.002 g of hydroquinone monomethyl ether. 7 g (55% of theory) of 2-perfluoroisopropylphenyl α-fluoroacrylate were obtained, boiling point 85° C. (under 1 mbar).

EXAMPLE 9

10 g (0.092 mol) of α-fluoroacryloyl chloride (obtained in accordance with example 1c) were added dropwise, at a temperature of 5° C., with stirring and in the course of 20 minutes, to a solution of 10.7 g (0.09 mol) of 4-cyanophenol and 9.1 g (0.09 mol) of triethylamine in 150 ml of anhydrous methylene dichloride, and the reaction mixture was then stirred for a further 30 minutes at the same temperature. The solid formed was filtered off and washed with 20 ml of anhydrous methylene dichloride. After 0.005 g of hydroquinone monomethyl ether had been added, the volatile constituents in the mixture of filtrate and wash solution were removed by distillation, and the residue was recrystallized from boiling n-hexane. 11.2 g (65% of theory) of 4-cyanophenyl α-fluoroacrylate were obtained, melting point 78° to 79° C.

EXAMPLE 10

10 g (0.092 mol) of α-fluoroacryloyl chloride (obtained in accordance with example 1c) were added dropwise, at a temperature of 5° C., with stirring and in the course of 20 minutes, to a solution of 16.7 g (0.089 mol) of 3,5-dichloro-4-hydroxybenzonitrile and 9 g (0.089 mol) of triethylamine in 200 ml of anhydrous methylene dichloride, and the reaction mixture was then stirred for a further 30 minutes at the same temperature. The solid formed was filtered off and washed with 20 ml of anhydrous methylene dichloride. After 0.005 g of hydroquinone monomethyl ether had been added, the volatile constituents in the mixture of filtrate and wash solution were removed by distillation, and the residue was recrystallized from boiling n-heptane. 18.7 g (81% of theory) of 2,6-dichloro-4-cyanophenyl α-fluoroacrylate were obtained, melting point 95° to 99° C.

EXAMPLE 11

10 g (0.092 mol) α-fluoroacryloyl chloride (obtained in accordance with example 1c) were added dropwise, at a temperature of 5° C., with stirring and in the course of 5 minutes, to a solution of 24.8 g (0.09 mol) of 3,5-dibromo-4-hydroxybenzonitrile and 9.1 g (0.09 mol) of triethylamine in 200 ml of anhydrous methylene dichloride, and the reaction mixture was then stirred for a further 30 minutes at the same temperature. The solid formed was filtered off and washed with 20 ml of anhydrous methylene dichloride. After 0.005 g of hydroquinone monomethyl ether had been added, the volatile constituents in the mixture of filtrate and wash solution were removed by distillation, and the residue was recrystallized from boiling n-heptane. 17.5 g (55% of theory) of 2,6-dibromo-4-cyanophenyl α-fluoroacrylate were obtained, melting point 135° to 138° C.

We claim:

1. A process for the preparation of a phenyl α-fluoroacrylate, which comprises reacting dropwise dimethyl α-fluoromalonate with an aqueous formaldehyde solution containing a basic catalyst, in a first process stage, thereby obtaining hydroxymethylated dimethyl α-fluoromalonate, then hydrolyzing, decarboxylating and dehydrating the resulting hydroxymethylated dimethyl α-fluoromalonate in a second process stage, and subsequently esterifying, in a third process state, the resulting α-fluoroacrylic acid (if appropriate in the form of an acid halide) with a phenol of the formula (2)

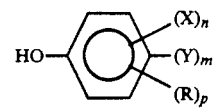

in which R denotes a halogenalkyl group having 1 to 8 carbon atoms and p is nought 1, 2, or 3, X denotes a halogen atom and n is nought or an integer from 1 to 5 (it being possible for X to denote different halogen atoms if n is greater than 1), Y denotes a hydrogen atom a cyano group, the radical X or the radical R and m is nought or 1, the sum of $n+m+p$ being 2 to 5.

2. The process as claimed in claim 1, wherein the first process stage is carried out at a temperature from 5° to 40° C., the second process stage is carried out at a temperature from 90° to 110° C., and the third process stage is carried out at a temperature from −10° to 50° C.

3. The process as claimed in claim 1, wherein the first process stage is carried out at 5° to 30° C.

4. The process as claimed in claim 1, wherein, in said first process stage, the hydroxymethylated dimethyl α-fluoromalonate is a solid under the reaction conditions.

5. The process as claimed in claim 4, wherein said solid is isolated from the first-stage reaction mixture by one or more of the following process steps: precipitation, salting out, or extraction with a water-immiscible organic solvent.

* * * * *